United States Patent [19]

Rabenau et al.

[11] Patent Number: 5,168,757
[45] Date of Patent: Dec. 8, 1992

[54] FLUID DISPLACEMENT AND PRESSURIZING DEVICE

[75] Inventors: Richard Rabenau, Arab; Rowland W. Kanner, Guntersville, both of Ala.

[73] Assignees: Ryder International Corporation, Arab, Ala.; Cordis Corporation, Miami Lakes, Fla. ; a part interest

[21] Appl. No.: 523,724

[22] Filed: May 15, 1990

[51] Int. Cl.⁵ .............................................. G01L 7/06
[52] U.S. Cl. ...................................... 73/714; 73/729; 604/99; 606/194
[58] Field of Search ................. 604/99, 224, 208, 209; 411/433, 437; 73/714, 756, 729; 128/344

[56] References Cited

U.S. PATENT DOCUMENTS

| | | | |
|---|---|---|---|
| 4,583,974 | 4/1986 | Kobernak | 604/99 |
| 4,715,378 | 12/1987 | Pope, Jr. et al. | 128/344 |
| 4,743,230 | 5/1988 | Nordquest | 604/99 |
| 4,777,951 | 10/1988 | Cribier et al. | 128/344 |
| 4,793,351 | 12/1988 | Landman et al. | 128/344 |
| 4,810,455 | 3/1989 | Pope, Jr. et al. | 264/273 |
| 4,838,864 | 6/1989 | Peterson | 604/100 |

FOREIGN PATENT DOCUMENTS

WO8909071 10/1989 PCT Int'l Appl. .

OTHER PUBLICATIONS

The Inflation Pro: A New Dual-Support System for Angioplasty.
USCI Wizard Disposable Inflation Device.

Primary Examiner—Donald O. Woodiel
Attorney, Agent, or Firm—Trexler, Bushnell, Giangiorgi & Blackstone, Ltd.

[57] ABSTRACT

The present invention provides an improved pressurization device for use with angioplasty balloon catheters, or the like. The device has a novel quick release mechanism which enables rapid advancement of a threaded screw plunger to attain initial pressurization, and then the subsequent engagement of said mechanism with the threaded surface of the plunger to achieve precise control during final pressurization of the balloon catheter. In addition, there is provided an improved and novel pressure indicating means for providing the physician with an analog readout of the pressure being applied to the balloon catheter.

10 Claims, 3 Drawing Sheets

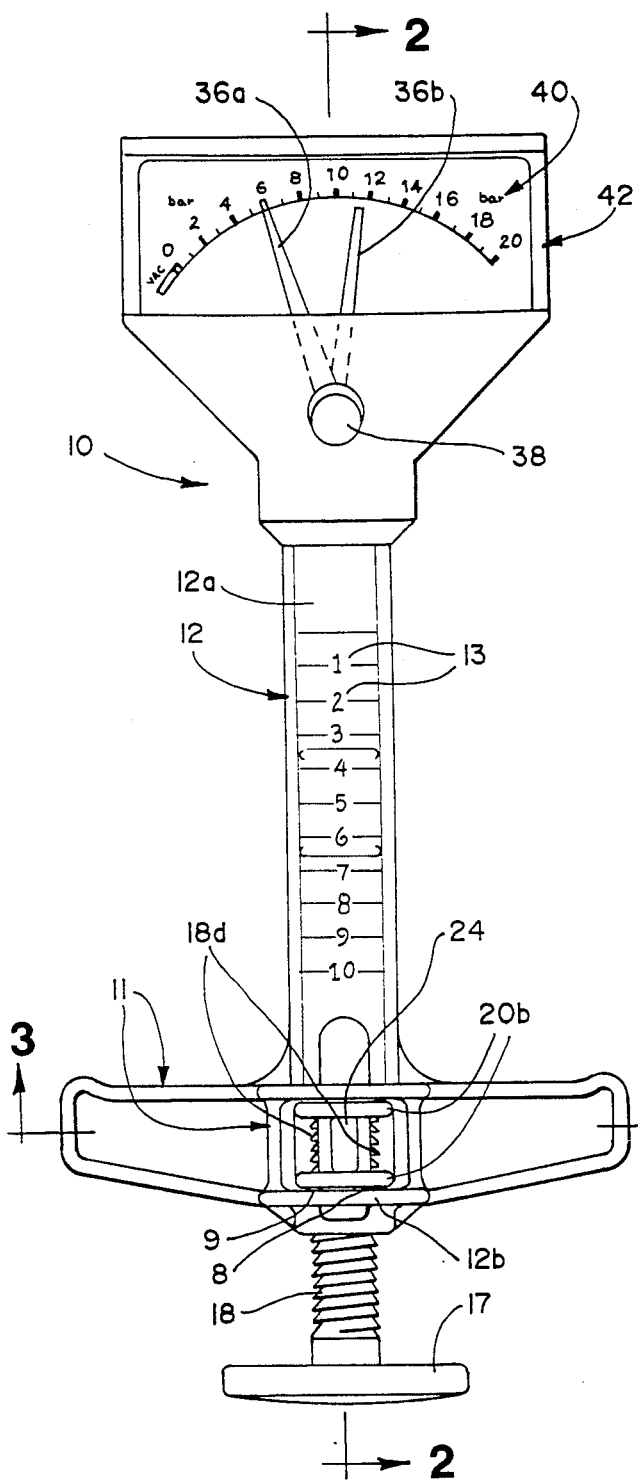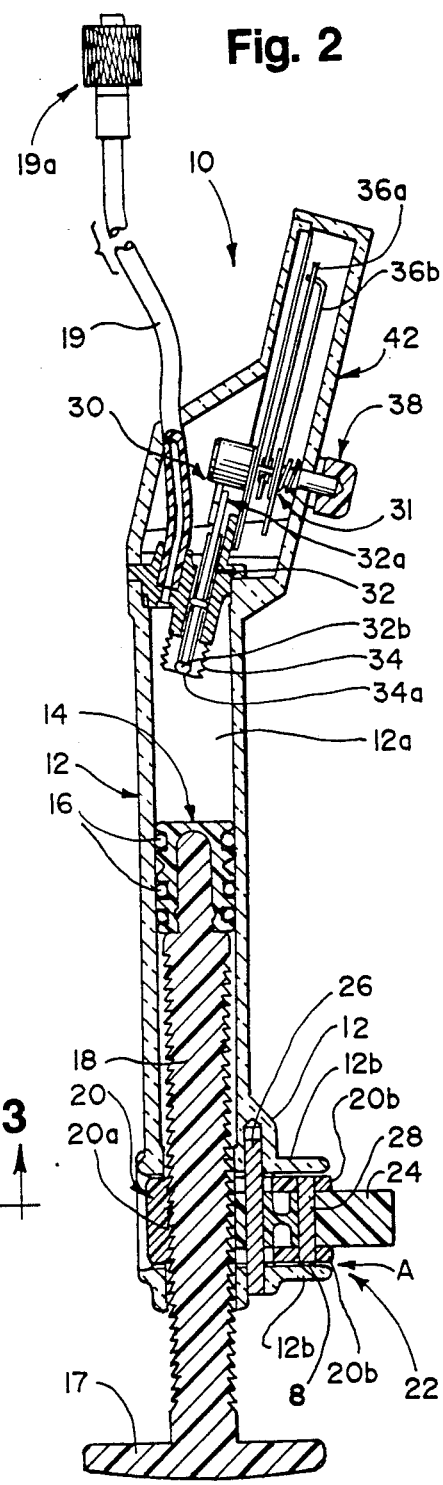

FLUID DISPLACEMENT AND PRESSURIZING DEVICE

BACKGROUND OF THE INVENTION

This invention relates to fluid pressurizing devices employing screw plungers, and more particularly relates to improved devices for actuating the screw plunger and monitoring the resulting fluid pressurization.

Fluid pressurization devices adapted for selectively applying and relieving a measured pressure on a closed volume of fluid have been developed for use in inflation and deflation for angioplasty balloon procedures interiorly of blood vessels. As described for example in U.S. Pat. No. 4,838,864, a syringe device inflates and deflates the catheterized balloon using a manually operated screw plunger to achieve or maintain specific pressure within the balloon which is monitored with an integral pressure gauge. The present invention provides an improved mechanism for attaining engagement and disengagement of the screw plunger as well as improved mechanism for monitoring the controlled fluid pressure.

SUMMARY OF THE INVENTION

The present invention provides an improved pressurization device for use with angioplasty balloon catheters, or the like. The device has a novel quick release mechanism which enables rapid advancement of a threaded screw plunger to attain initial pressurization, and then the subsequent engagement of said mechanism with the threaded surface of the plunger to achieve precise control during final pressurization of the balloon catheter. In addition, there is provided an improved and novel pressure indicating means for providing the physician with an analog readout of the pressure being applied to the balloon catheter.

In accordance with the present invention, a release mechanism particularly adapted for angioplasty inflator devices which enable rapid and selective movement of a threaded screw plunger and nut member combination into or out of threaded engagement, which release mechanism comprises a housing and threaded screw means slidably displaceable through the housing. The nut member has only partial threads and is pivotally engageable and disengageable with the threaded screw means by a pivot structure which is itself pivotally mounted on a first pivot bearing secured on the housing and coupled to the nut member for the selectively threaded engagability with the screw.

In a preferred embodiment, the nut member is bifurcated to provide a pair of opposingly spaced mounting portions extending from the threaded portion and partial threads. The mounting portions include respective apertures through which the first pivot bearing extends. A manually operated pivotal lever is positioned between the spaced mounting portions of the nut and a second pivot bearing extends between the mounting portions for pivot of the lever relative to the mounting portions such that the second pivot bearing pivots with respect to the first pivot bearing when the lever is manually pivoted. The dual pivot bearing structure enables the manual pivot of the lever to produce a rolling pivot and translation of the nut in the selective displacement of the partial nut threads between the positions of engagement and disengagement with the screw. Each of the apertures through the nut mounting portions includes first and second notches within which the first pivot bearing is lodged to releasably lock the respective engaged and disengaged positions of the partial nut threads. The bifurcated nut structure and straddled toggle lever provide constant, self-alignment with the screw, and the peripheral edges of the nut apertures provide low-friction, cammed guidance of the combined pivot end translation of the nut structure so that the notches lock the respective engaged and disengaged nut positions, reinforced by low-friction detents.

The preferred embodiment of the inflator device also includes a cylinder and fluid displacement piston mounted on the end of the screw by mating, snap-action, interference coupling for enabling displacement of the piston without rotation relative to the threaded rotation of the screw displacement in order to prevent any fluid leakage between the piston and the cylinder. The preferred inflator device also includes an integral pressure gauge which is isolated from the pressurized fluid and is linked to a bellows structure which is externally exposed to the pressurized fluid and responds to the pressure with linear collapse and expansion of the bellows structure which is transmitted through the linkage to the monitoring gauge. In comparison with prior art devices which use a bourdon tube type pressure gauge, the stainless steel bellows structure and isolated gauge eliminate potential contaminants therefrom in the pressurized fluid as well as any dead air spaces which could generate air bubbles particularly hazardous to use of the pressurized fluid for angioplasty balloon inflation and deflation. Contaminants in the fluid are of critical concern, since balloon catheters have been known to rupture in use and thus introducing the fluid medium and any contaminants or air bubbles into the blood stream. Thus, the fluid medium which is normally sterile saline must be kept contaminant and air bubble free.

BRIEF DESCRIPTION OF THE DRAWINGS

FIG. 1 is a top plan view of one embodiment of an inflator device in accordance with the present invention;

FIG. 2 is a sectional view along a plane indicated as line 2—2 in FIG. 1;

DESCRIPTION OF THE ILLUSTRATED EMBODIMENT

Figure 3:
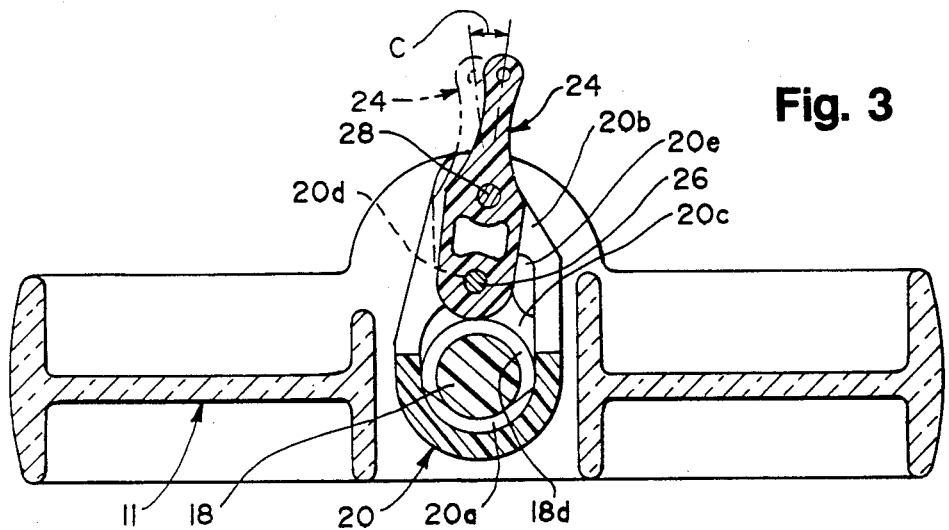
FIG. 3 is a sectional view taken along a vertical plane indicated at line 3—3 in FIG. 1.

Referring to FIGS. 1 and 2, an embodiment of the inflator device in accordance with the present invention is designated generally by reference character 10. The inflator device 10 has a generally cylindrical syringe body and fluid displacement chamber 12, with integral handle 11, which chamber 12 is transparent for viewing the fluid within the cavity 12a during fluid aspiration or dispensing. Accordingly, the syringe body 12 is molded, with volumetric indicia 13, for transparency from polycarbonate or similarly suitable resins. A piston 14 is slidably displaceable within the syringe body 12 and carries a pair of peripherally mounted O-ring fluid seals 16 for pressure retention and the prevention of leakage past the piston 14. The chamber 12a communicates with a fluid tube 19 that may be operatively coupled to the balloon catheter structure (not shown) by means of a fluid connection or fitting 19a. At the forward end of the unit is the pressure monitoring means 30 which provides the physician with an indication of the pressure in the chamber 12a. The pressure monitoring means of the preferred form of the invention attains performance and safety advantages over the prior art, and will be discussed in greater detail hereinafter.

Figure 7:
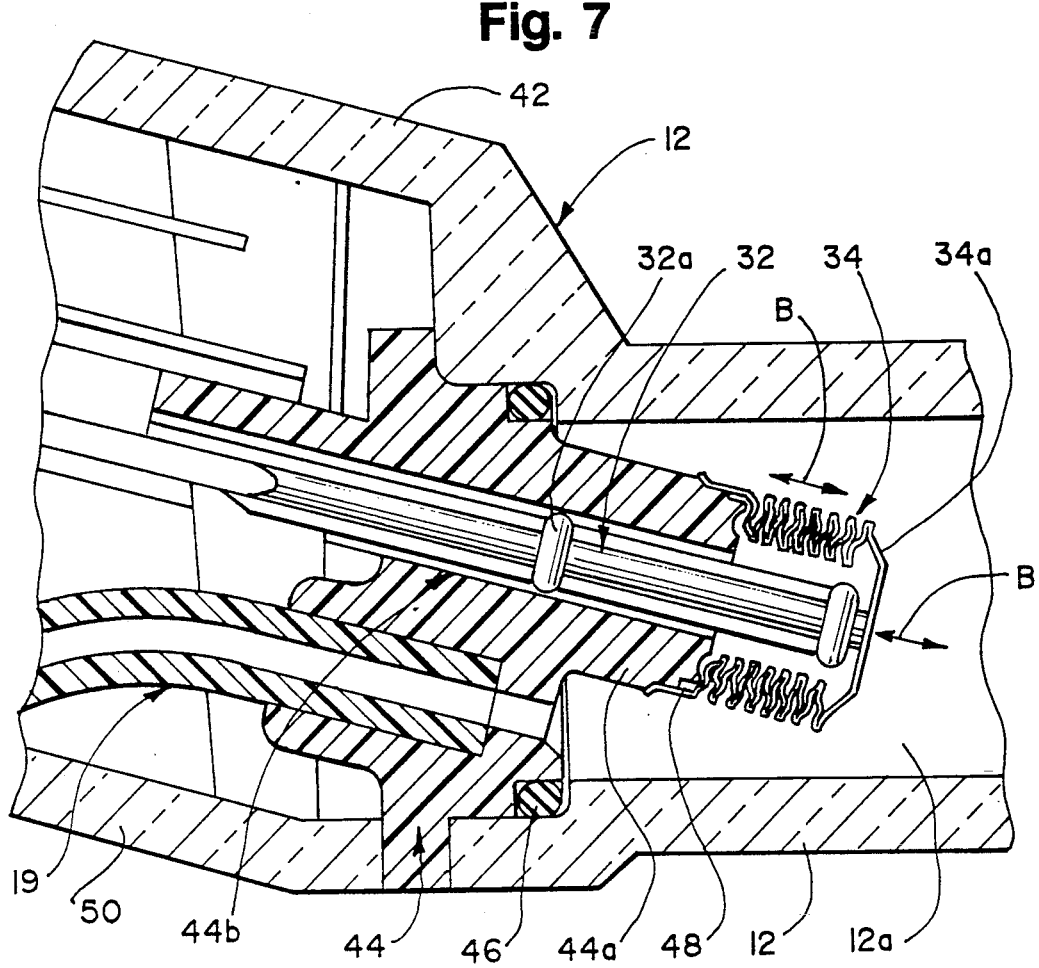
FIG. 7 is an enlarged, fragmentary sectional view of the pressure translation linkage portion of the inflator device shown in FIG. 2.
Figure 8:
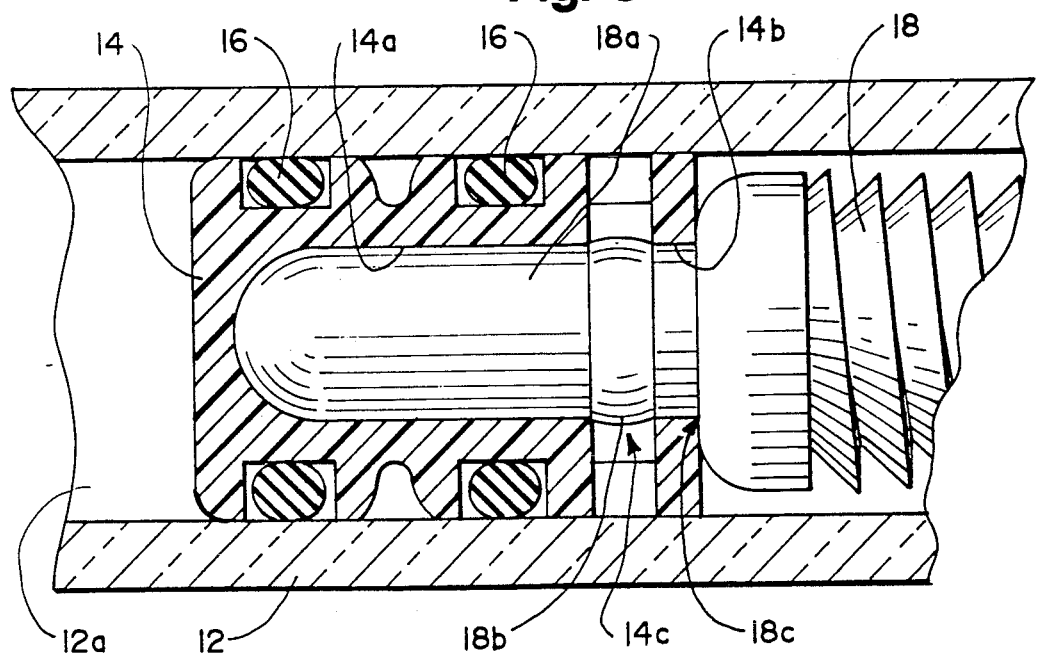
FIG. 8 is an enlarged, fragmentary sectional view of the piston portion of the inflator device shown in FIG. 2.

As best shown in FIG. 7, piston 16 is mounted on an unthreaded, pilot nose end 18a of a threaded screw plunger 18. The screw plunger 18, FIG. 1, has an integral palm knob 17 to facilitate movement thereof. The pilot nose end 18a freely rotates within a central journal cavity 14a of the piston 14. The rear end of the piston 14 has an axial entrance opening 14b through which the pilot end nose 18a passes into the cavity 14a, and then intermediate annular collar portion 18b has a slightly larger diameter than both the pilot nose end 18a and the piston opening 14b. Collar 18b is forced through opening 14b into an annular clearance space 14c when the piston 14 is mounted on the pilot nose end 18a in a snap-action, interference coupling which prevents the collar 18b from withdrawing or backing out through the entrance opening 14b when the screw 18 is retracted aspirate fluid into the cavity 12a, as more fully described hereinafter. Thus, the pilot nose end 18a, collar 18b and thrust surface 18c are freely rotatable relative to the coupled piston 14 so that the piston is linearly advanced or retracted without rotation relative to the rotation of the screw 18 in threaded advancement or retraction, in order to prevent any leakage of pressurized fluid from the cavity 12a between the piston O-rings 16 and the syringe body 12.

Figure 4:
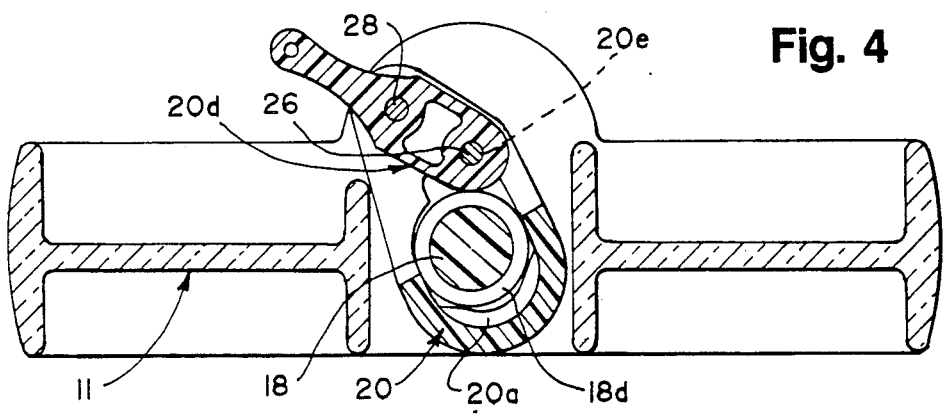
FIG. 4 is a sectional view similar to FIG. 3 and showing pivoted position of a manual lever and coupled nut structure.
Figure 5:
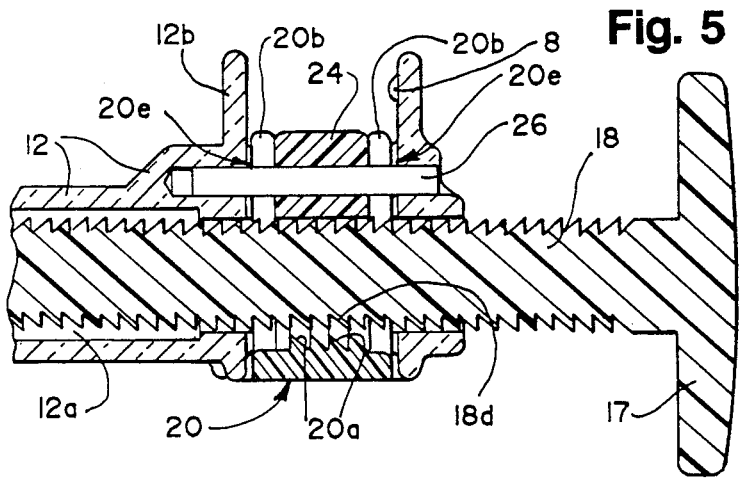
FIG. 5 is an enlarged, fragmentary sectional view similar to the lower portion of FIG. 2 with the exception that the manual lever and nut structure are shown in the pivoted position corresponding to FIG. 4.
Figure 6:
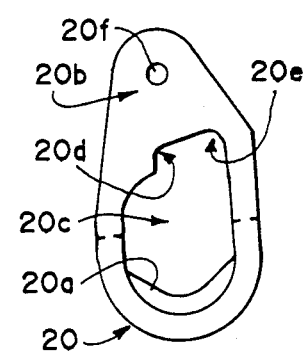
FIG. 6 is a side elevational view of the nut structure shown in FIGS. 1-5.

Referring again to FIGS. 1 and 2, a nut structure generally designated by reference character 20 is mounted in the rearward portion of the syringe body 12 and has partially formed threads 20a which are selectively engageable and disengageable from the screw threads 18d or screw 18 by displacement of the entire nut structure 20 in a combined pivotal and translational motion as best shown in FIGS. 4 and 5, in comparison with the threaded engagement of the nut and screw threads 20a, 18d shown in FIG. 3. The nut structure 20 and threads 20a are selectively disengaged from the screw 18 in order to permit manual rapid displacement of the screw 18 and piston 14 particularly for aspiration of saline solution into the syringe cavity 12a from the coupled tube and connected saline supply reservoir (not shown). The disengagement of the nut and threads 20a also enable a rapid advancement of the screw 18 and piston 14 to discharge solution from the cavity 12a through tube 19, when the tube 19 is connected to inflate an angioplasty balloon (not shown, which has been previously positioned within a blood vessel or heart valve using a balloon catheter). Rapid retraction of the screw 18 and piston 14 also enable swift aspiration of the fluid into the cavity 12a for rapid deflation of a balloon. Also, prior to connection to the catheter, the screw 18 may be operative to insure that all air bubbles have been eliminated from the sterile saline fluid within the unit 10 and the attached fluid tube 19. As previously mentioned, the transparency of the syringe body 12 enables visual confirmation that no air bubbles have been drawn with fluid supply aspiration into the cavity 12a, or if drawn, bubbles have been eliminated.

In order to enable the selective engagement (FIG. 3) or disengagement (FIG. 4) of partial nut threads 20a with the screw threads 18d, the nut structure 20 is selectively displaceable by manually activating a nut release mechanism generally designated by reference character 22 in FIG. 2. The release mechanism 22 is mounted between a pair of spaced flanges 12b transversely extending from the syringe body 12. The release mechanism 22 is activated by a manual toggle lever 24 which is selectively pivoted on a primary pivot bearing pin 26 which is secured within the syringe body 12 and bridges the base of the spaced flanges 12b as best shown in FIG. 5.

As viewed in FIGS. 3, 4 and 5, the nut structure 20 includes partial teeth 20a formed in a lower base portion and also includes an upstanding, bifurcated portion forming a pair of spaced, elongate arm or mounting portions 20b. The mounting portions 20b each have a large aperture 20c through which the primary bearing pin 26 extends so that the nut structure 20 engages but is not pivotally supported on the primary pivot pin 26.

A secondary pivot pin 28 extends through the lever 24, and the ends of the secondary pivot pin 28 are secured or journaled in the opposing nut mounting portions 20b so that the lever 24 and nut 20 are pivotally coupled by the pin 28. The pivotal motion of the lever 24 is constrained by the primary pivot bearing pin 26 on which the lever is pivotally supported and secured to the syringe body 12. Accordingly, when the nut structure 20 is most tightly engaged with the screw 18 as shown in FIG. 3, the lever 24 is vertically positioned as shown in dashed lines, so that the secondary pivot pin 28 is vertically aligned over the primary pivot pin 26 and screw 18. However, the lever 24 is further pivoted "over center" at a small angle C from vertical into a locked position of the nut structure which is releasably locked by engagement of the primary pivot bearing pin 26 within a first notch 20d formed in the nut aperture 20c. Additional releasable locking is provided by engagement of a small detent bump 8 projecting from at least one of the syringe body flanges 12b which releasably extends into an end opening of the journaling bore 20f of the mounting portion 20b through which the secondary pivot bearing pin 28 extends and is aligned in the over center locking position of the lever 24 for the nut engagement. The over center locking position of the lever 24 insures that any slight motion of the lever 24 which could be induced by the fluid pressure in the cavity 12a imposed on the screw 18 will be a displacement of the lever 24 toward the vertical position of the lever 24 resulting in tighter engagement of the screw 18 and nut structure 20 rather than any tendency for loosening or disengagement thereof.

In order to release the threaded engagement of the nut structure 20 from the screw 18 for rapid displacement of the screw and piston 14 as previously described, the lever 24 is manually pivoted with sufficient force to release the detent 8 from the bore opening 20f so that the lever 24 pivots to the left from the position shown in FIG. 3 to the position shown in FIG. 4 resulting in a rolling pivot of the nut structure 20 (coupled to the lever 24 by the pin 28); the rolling pivot of the nut structure is guided by sliding engagement of the peripheral, camming surface of the nut aperture 20c against the stationary, primary pivot bearing pin 26, from the notch 20d into the notch 20e. The movement of the nut structure 20 and the notches 20d and 20e against the pin 26 produces both a counterclockwise rotation of the partial nut threads 20a as well as a downward translation disengaging the nut threads 20a from the screw threads 18d as the pin 26 lodges within the displaced notch 20e tending to releasably lock the resulting disengaged position of the nut structure 20.

A second detent 9 is located on the flange 12b for insertion into the bore opening 20f as the counterclockwise pivot of the lever 24 and nut structure 20 reaches the position in FIG. 4. Nut structure 20 is mounted between the flanges 12b with the slight clearance space A to allow slight axial movement of the nut structure 20 forced by the sliding interference by the detents 8 and 9 during the pivotal motions of the lever 24 and the nut structure 20 between the engaged and disengaged positions (FIG. 3, FIG. 4) of the nut structure. Clearance space A also enables the slight axial displacement of the nut structure 20 to provide self-alignment of the partial nut threads 20a during a reengagement with the screw threads 18d. Accordingly, when the disengaged nut structure 20 in the position of FIG. 4 is to be reengaged with the screw 18 in the position of FIG. 3, after completion of the desired rapid displacement of the screw and piston 14, the toggle lever 24 is manually rotated clockwise which elevates and rotates the nut structure 20 so that the notches 20e and 20d are displaced and the bearing pin 26 lodges within the notch 20d to provide locking of the nut structure in the engaged position aided by removal of the bore opening 20f from the detent 9 and realigned reception of the upper detent 8. Thus, the bifurcated nut structure 20 and straddled toggle lever 24 provide constant, self-alignment with the screw. The peripheral edges of the nut apertures 20c provide low-friction, cammed guidance of the combined pivot and translation of the nut structure 20 so that the notches 20e and 20d lock the respective engaged and disengaged nut positions, reinforced by the low-friction detents 8 and 9.

Referring again to FIGS. 1 and 2, the fluid pressure within the syringe cavity 12a is monitored by a pressure sensing or indicating means generally designated by reference character 30. The pressure sensing means as disclosed utilizes a gauge movement 31 which is isolated from the fluid within the cavity 12a. This isolation eliminates any contamination of the fluid with particulate or dissolved materials such as salts or fluxes to which the fluid is exposed in previously employed bourdon-type pressure gauge and connections which also create a source of dead air space promoting entry of air bubbles into the cavity 12a with consequent air bubble hazards in angioplasty balloon inflation procedures. The movement 31 is coupled to one end 32a of a pressure transmission linkage rod 32. The opposite end 32b of the rod is secured internally to the pressure registration face 34a of a bellows structure 34. The bellows structure 34 is preferably fabricated from stainless steel to prevent contamination of the exposed fluid. As best shown in FIG. 7, the bellows structure 34 projects into fluid cavity 12a but is internally isolated from the pressurized fluid. The pressure registration surface 34a is externally exposed to the fluid pressure condition within the cavity 12a and responds to the pressure with linear displacement and consequent reversible expansion or collapse of the bellows structure 34 as indicated by arrows B. The coupled linkage rod 32 therefore transmits the linear displacement of the pressure registration surface 34a to the gauge 31 which converts the linear rod movement into rotary movement of the indicator needle 36a. A second needle 36b in the form of a "telltale" may be employed which is operatively coupled to a reset knob 38. Thus, as the gauge mechanism 31 moves the needle 36a, needle 36a will engage and move the telltale needle 36b which holds its position once the balloon catheter is depressurized thus recording the highest pressure indicated by the needle 36a until reset knob 38 is actuated. Suitable gauge movements 31 are commercially available from Medi-Gauge Inc. of Bloomington, Minn. and Toomey Engineering Systems Co., Inc. of Westfield, Mass.

In order to enable maximum light transmission and visibility of the pressure meter display 40, particularly during darkened surgery room conditions to promote visibility of ultrasound or X-ray monitors, the display housing generally designated by reference character 42 including both cover and sides, is transparent and preferably integrally molded with the syringe body 12 with a small degree of inclination as shown in FIG. 2, to promote visibility convenience.

Referring again to FIG. 7, a sealed coupling of the fluid tube 19 is provided by an integrally molded plug member 44 which carries an O-ring 46 to close and seal the mouth end of the syringe barrel 12. In addition, the plug 44 provides a cylindrical mounting portion 44a which supports the rear end of the bellows structure and a bore 44b through which the transmission linkage rod 32 and guide rings 32a are displaced. The bottom of the plug is secured by a bottom wall 50 which also provides the lower wall of the gauge housing 42 through which the fluid tube 19 passes to a coupler 19a for connection for example to a fluid supply or angioplasty balloon.

In summary of operation, the inflator device is primed with a sterile saline solution aspirated into the cavity of the syringe body after which the supply tube is disconnected and coupled to a balloon catheter which has been previously positioned within a blood vessel as for example a heart valve or in the approximate area of an artery or vein that is blocked with plaque. The syringe plunger is then advanced and retracted for selectively applying and relieving fluid pressure to the balloon, in a repetitive manner which is facilitated by both a rapid sliding of the screw plunger and a slower threaded displacement of the screw plunger enabled by the quick release mechanism for the actuating selective engagement and disengagement of the nut structure with the screw plunger. The pressure is accurately monitored during the angioplasty procedure by the incorporated pressure gauge which is isolated from the pressurized fluid.

In light of the foregoing description of one embodiment in accordance with the present invention, modifications will be evident, for example the pressure monitoring gauge can be detached from the syringe body for use as a separate unit. In addition, the bellows structure could be modified for internal pressurization by the monitored fluid. Furthermore, the linear motion of the bellows structure can be converted to analog or digital electronic display either directly or through a mechanical amplifying linkage to actuate a linear variable directional transducer (LVDT) or a linear taper conductive plastic strip such as that manufactured by Waters Manufacturing Inc. of Wayland, Mass., or by a precise rheostat. In a further alternative, a standard pressure transducer might also be employed by means of direct communication via a through-port in the chamber wall or by mounting the transducer behind a thinly molded section in the chamber wall which would serve as a septum to prevent contamination of the transducer or leakage of the saline fluid contained within the device. Accordingly, all such modifications are within the broad scope of the appended claims and equivalents thereof.

The invention is claimed as follows:

1. An actuating mechanism for rapidly and selectively moving a threaded screw and nut member combination into or out of threaded engagement, particularly for use of the screw as a controlled fluid plunger, comprising:
   a housing and threaded screw means slidably displaceable through said housing;
   a nut member having only partial threads pivotally engageable and disengageable with said threaded screw means;
   and pivot means pivotally mounted on a pivot bearing secured on said housing, and coupled to said nut member for pivot of said pivot means and nut member in order to displace said nut member for said selectively threaded engagability with said screw means, said pivot means further including a manually operated lever member and wherein said nut member further includes a mounting portion to which said lever portion is coupled for manually pivoted displacement of said partial nut threads, wherein said lever member is pivotally secured on a second pivot bearing coupled on said mounting portion of said nut member in order to enable pivot of said lever member with respect to said mounting portion simultaneously with pivot of said lever member and nut member during said displacement of said partial threads.

2. An actuating mechanism for rapidly and selectively moving a threaded screw and nut member combination into or out of threaded engagement, particularly for use of the screw as a controlled fluid plunger, comprising:
   a housing and threaded screw means slidably displaceable through said housing;
   a nut member having only partial threads pivotally engageable and disengageable with said threaded screw means;
   and pivot means pivotally mounted on a pivot bearing secured on said housing, and coupled to said nut member for pivot of said pivot means and nut member in order to displace said nut member for said selectively threaded engagability with said screw means, wherein said nut member displaceably floats with respect to said first pivot bearing in order to enable both translation and rotation of said nut member and partial threads with respect to said first pivot bearing and screw means.

3. A mechanism according to claim 2, wherein said nut member includes guide means for guiding said floating displacement with respect to said first pivot bearing.

4. A mechanism according to claim 3, wherein said guide means comprises a cam surface for slidable engagement against said first pivot bearing during said nut member displacement.

5. A mechanism according to claim 4, wherein said cam surface comprises a peripheral surface formed on an aperture in said nut member through which said first pivot bearing extends.

6. An actuating mechanism for rapidly and selectively moving a threaded screw and nut member combination into or out of threaded engagement, particularly for use of the screw as a controlled fluid plunger, comprising:
   a housing and threaded screw means slidably displaceable through said housing;
   a nut member having only partial threads pivotally engageable and disengageable with said threaded screw means;
   and pivot means pivotally mounted on a pivot bearing secured on said housing, and coupled to said nut member for pivot of said pivot means and nut member in order to displace said nut member for said selectively threaded engagability with said screw means, wherein said nut member comprises a bifurcated portion defining a pair of opposingly spaced mounting portions extending from a threaded portion including said partial threads, said mounting portions including respective apertures through which said first pivot bearing extends, and wherein a lever member is disposed between said spaced mounting portions and a second pivot bearing extends between said mounting portions for pivot of said lever member relative to said nut member such that said second pivot bearing pivots with respect to said first pivot bearing during pivot of said lever member and said selective displacement of said partial nut threads.

7. An actuating mechanism for rapidly and selectively moving a threaded screw and nut member combination into or out of threaded engagement, particularly for use of the screw as a controlled fluid plunger, comprising:
   a housing and threaded screw means slidably displaceable through said housing;
   a nut member having only partial threads pivotally engageable and disengageable with said threaded screw means;
   and pivot means pivotally mounted on a pivot bearing secured on said housing, and coupled to said nut member for pivot of said pivot means and nut member in order to displace said nut member for said selectively threaded engagability with said screw means, wherein said pivot means is releasably pivotable to an over center position and said pivot means and nut structure each have respective configurations in which said nut structure is in threaded engagement with said screw such that axial force on said screw means promotes tighter radial engagement with said nut structure.

8. An actuating mechanism for rapidly and selectively moving a threaded screw and nut member combination into or out of threaded engagement, particularly for use of the screw as a controlled fluid plunger, comprising:
   a housing and threaded screw means slidably displaceable through said housing;
   a nut member having only partial threads pivotally engageable and disengageable with said threaded screw means;
   pivot means pivotally mounted on a pivot bearing secured on said housing, and coupled to said nut member for pivot of said pivot means and nut member in order to displace said nut member for said selectively threaded engagability with said screw means; and a fluid displacement chamber secured on said housing and through which fluid is displaced by piston means secured on said screw means, during rapid displacement of said screw means when said nut member is disengaged therefrom or during slower, threaded displacement of said screw means when said nut member is threaded thereto, wherein said piston means is coupled to the end of said screw means by mating, snap-action interference coupling means formed on said piston and screw end for enabling displacement of said piston means without rotation relative to rotation of said screw means during threaded displacement thereof, in order to prevent any fluid leakage between said piston means and chamber.

9. An actuating mechanism for rapidly and selectively moving a threaded screw and nut member combination into or out of threaded engagement, particularly for use of the screw as a controlled fluid plunger, comprising:

a housing and threaded screw means slidably displaceable through said housing;

a nut member having only partial threads pivotally engageable and disengageable with said threaded screw means;

pivot means pivotally mounted on a pivot bearing secured on said housing, and coupled to said nut member for pivot of said pivot means and nut member in order to displace said nut member for said selectively threaded engagability with said screw means; and a fluid displacement chamber secured on said housing and through which fluid is displaced by piston means secured on said screw means, during rapid displacement of said screw means when said nut member is disengaged therefrom or during slower, threaded displacement of said screw means when said nut member is threaded thereto, and a linkage assembly for transmission of fluid pressure within said chamber including a collapsible and expandable bellows structure having a pressure registration surface displaceable along a generally linear, axial path with said expansion and collapse; and a transmission member coupled to said registration surface and displaceable therewith for indication of the degree of pressure imposed on said registration surface reflected by the displacement of the transmission member.

10. A mechanism according to claim 9, wherein said transmission member comprises a rod member one end of which is secured to said registration surface and a second end thereof is coupled to gauge means for representing the degree of pressure indicated by displacement of said transmission rod member.

* * * * *

UNITED STATES PATENT AND TRADEMARK OFFICE
CERTIFICATE OF CORRECTION

PATENT NO. : 5,168,757
DATED : December 8, 1992
INVENTOR(S) : Richard Rabenau, Rowland W. Kanner It is certified that error appears in the above-identified patent and that said Letters Patent is hereby corrected as shown below:

On the title page: Item [73]:
Assignees: "Ryder International Corporation, Arab, Ala.; Cordis Corporation, Miami Lakes, Fla.; a part interest"

it should read: -- Ryder International Corporation, Arab, Ala. --

Signed and Sealed this

Twenty-ninth Day of March, 1994

Attest:

BRUCE LEHMAN

*Attesting Officer*     *Commissioner of Patents and Trademarks*